United States Patent [19]

Thurber et al.

[11] Patent Number: 5,710,281
[45] Date of Patent: Jan. 20, 1998

[54] ORGANIC COMPOUNDS SUITABLE AS REACTIVE DILUENTS AND BINDER PRECURSOR COMPOSITIONS INCLUDING SAME

[75] Inventors: Ernest L. Thurber, St. Paul; Eric G. Larson, Lake Elmo; Alan R. Kirk, Cottage Grove; Gregg D. Dahlke, St. Paul, all of Minn.

[73] Assignee: Minnesota Mining and Manufacturing Company, St. Paul, Minn.

[21] Appl. No.: 606,325

[22] Filed: Feb. 23, 1996

Related U.S. Application Data

[60] Division of Ser. No. 334,817, Nov. 4, 1994, Pat. No. 5,523,152, which is a continuation-in-part of Ser. No. 143,824, Oct. 27, 1993, abandoned.

[51] Int. Cl.$^6$ ............... C07D 487/04; C07D 209/48; B32B 5/16; B32B 18/04
[52] U.S. Cl. ............... 548/429; 548/433; 548/513; 428/323; 428/325; 428/329; 428/331
[58] Field of Search .................. 548/451, 485, 548/513, 429, 433; 428/323, 325, 329, 331

[56] References Cited

U.S. PATENT DOCUMENTS

| | | | |
|---|---|---|---|
| 2,882,262 | 4/1959 | Smith et al. | 260/80.5 |
| 4,179,478 | 12/1979 | Rosenkranz et al. | 525/113 |
| 4,180,474 | 12/1979 | Schuster et al. | 252/188.3 R |
| 4,382,135 | 5/1983 | Sinka et al. | 526/301 |
| 4,588,419 | 5/1986 | Caul et al. | 51/295 |
| 4,591,651 | 5/1986 | Delmas et al. | 549/473 |
| 4,903,440 | 2/1990 | Larson et al. | 51/298 |
| 5,047,259 | 9/1991 | Oberkobusch et al. | 427/27 |
| 5,047,261 | 9/1991 | Moussa et al. | 427/54.1 |
| 5,055,113 | 10/1991 | Larson et al. | 51/298 |
| 5,143,954 | 9/1992 | Hutton et al. | 524/106 |
| 5,178,646 | 1/1993 | Barber, Jr. et al. | 51/298 |
| 5,192,815 | 3/1993 | Okada et al. | 523/115 |
| 5,217,994 | 6/1993 | Egbertson et al. | 514/484 |
| 5,236,472 | 8/1993 | Kirk et al. | 51/298 |

FOREIGN PATENT DOCUMENTS

| | | | |
|---|---|---|---|
| 0 222 059 | 7/1986 | European Pat. Off. | |
| 0 222 059 | 5/1987 | European Pat. Off. | |
| 0 400 658 A3 | 5/1990 | European Pat. Off. | |
| 0 400 785 | 12/1990 | European Pat. Off. | |
| 0 400 785 | 9/1995 | European Pat. Off. | |
| 43-133491 | 12/1974 | Japan | |
| 59-171948 | 9/1984 | Japan | G03C 1/68 |
| 02000603 A2 | 1/1990 | Japan | |
| 4 308 578 | 10/1992 | Japan | |
| 930 668 | 7/1963 | United Kingdom | |
| 930668 | 7/1963 | United Kingdom | |
| WO 88/09783 | 12/1988 | WIPO | C07C 69/84 |

OTHER PUBLICATIONS

Derwent Abstract Accession No. 75–20159W [12] for Japanese Patent No. 49133491 A (Dec. 21, 1974).
WPAT Abstract Accession No. 89–327660/45 for Japanese Patent No. J01242569–A (Sep. 27, 1989).
WPAT Abstract Accession No. 91–129156/18 for Japanese Patent No. J03068609–A (Mar. 25, 1991).
Chemical Abstract No. 93:96890j for Photochemical Hardening of Oligoester Maleate Compositions in an Air Medium. vol. 93, 1980.
Decker and Moussa, *Photopolymerization of Multifunctional Monomers*, Jul. 17, 1990—English Translation of full article provided.
Chemical Abstracts, 172726a Crosslink–hardenable Resin Compositions, 42–Coatings, vol. 82, 1975, p. 99.
Chemical Abstracts, 140208j Acryloyloxyalkyl Benzoate–acrylate Copolymers as Ultraviolet Light Absorbers and a Method for Their Preparation, 62–Essential Oils, Cosmetics, vol. 111, 1989 p. 381.
D'Alelio et al., Journal of Polymer Science: Part A–1, vol. 5, (1967) pp. 287–321.
Henry Feuer and Una E. Lynch, *Synthesis and Reaction of Unsaturated N–Methlolamides*, "The Synthesis and Reactions of Unsaturated N–Methylolamides," Oct. 20, 1953, vol. 75, pp. 5027–5029.
Derwent Publications Ltd., London, GB; AN 91–345126 C47!—Abstract of SU A,1 634 465 (Spetstekhnosnastka), Mar. 15, 1991.
Jan. 1993, Photomer Radiation Curing Chemicals Product Description Listing.
Chemical Abstracts, 170610x Imido(meth)acrylates and Resin Compositions and Solder Resists Containing Them, 76–Electric Phenomena, vol. 112, 1990 pp. 847–848.
Chemical Abstracts, 7996b Resin Compositions and Heat–Resistant Coatings for Optical Fibers, 42–Coatings, vol. 116, 1992.
Chemical Abstracts, 3378s Phthalimide Derivatives, 27–Heterocycles, vol. 80, 1974 p. 295.
Sartomer Product Catalog, 1992, Sartomer Company, Inc., pp. 6–7.
Material Safety Data Sheet for "Photomer 6173", Diamond Shamrock Chemicals Company, 1981.
Derwent Publications, Inc. 88–368605/51 (1987).
STN International Registry File Search Statistics, 24 Nov. 1992. pp. 1–55.

*Primary Examiner*—Johann Richter
*Assistant Examiner*—Laura Lutz
*Attorney, Agent, or Firm*—Doreen S. L. Gwin

[57] ABSTRACT

Organic compounds having at least one ethylenically-unsaturated group are described, the organic compounds being suitable for use in coatable compositions as reactive diluents; compounds of the invention preferably have a divalent organic linking moiety devoid of reactive groups other than optional ethylenically-unsaturated groups, and a polar organic moiety and are particularly adept in solubilizing aminoplast resins having radiation-curable pendant groups.

9 Claims, No Drawings

ORGANIC COMPOUNDS SUITABLE AS REACTIVE DILUENTS AND BINDER PRECURSOR COMPOSITIONS INCLUDING SAME

This is a divisional application of U.S. Ser. No. 08/334,827, now U.S. Pat. No. 5,523,152 Nov. 4, 1994, which is a continuation-in-part of U.S. Ser. No. 08/143,824, filed Oct. 27, 1993 now abandoned.

FIELD OF THE INVENTION

This invention relates to curable ethylenically-unsaturated diluents for resin systems and the resin systems which contain them.

BACKGROUND OF THE INVENTION

Ethylenically-unsaturated compounds that are free-radically curable by either irradiative (UV, electron beam) or thermal means, and that are capable of reducing the viscosity of a second ethylenically-unsaturated resin species for easier coating, casting, molding, and the like, are referred to as "reactive diluents." When the particular method of curing is irradiative, the materials may be known as "radiation-curable diluents" or "radiation-hardenable diluents." Often, the diluents copolymerize with ethylenic unsaturation in the second resin species to effect crosslinking and, the effect most usually sought, hardening or toughening of the resin.

Reactive diluents play a crucial role in binder precursor compositions used in the production of abrasive articles, in that the binder precursor compositions are typically very viscous and conventionally diluted with an appropriate solvent, usually an organic solvent, prior to coating or casting. The use of such solvents is increasingly undesirable from both environmental and human health viewpoints. Reactive diluents provide a means of decreasing the viscosity of the binder precursor composition to the point of convenient coatability without adding undesirable solvents, thus providing 100% solids resin compositions. (As used throughout this disclosure, the term "100% solids resin" means that substantially all, and preferably all of the liquid components of the binder precursor composition are reacted with the other ingredients of the binder precursor composition, i.e., there are substantially no volatile organic compounds which are emitted during the curing of the binder precursor composition.) See, e.g., assignee's U.S. Pat. No. 5,178,646.

To be commercially useful, reactive diluents for binder precursor compositions useful in the abrasives art preferably exhibit a combination of properties: adequate solvency of the resin(s); rapid cure rate; contribution to, or at least no diminution of, the final hardness of the cured system; and, of course, low cost.

A class of aminoplast hard resins particularly useful in the formation of the make coating, size coating, both coatings, or as a backing treatment of a coated abrasive backing, or in fibrous non-woven abrasive products is described in U.S. Pat. Nos. 4,903,440; 5,055,113; and 5,236,472; all of which are incorporated by reference herein. Aminoplast resins have at least one pendant unsaturated group per molecule or oligomer, and therefore may be cured using radiation energy. These unsaturated groups are preferably positioned α,β with respect to the carbonyl moiety, and can be acrylate, methacrylate or acrylamide type groups. Such resins are obtained in general by the reaction of amino compounds with aldehydes to produce compounds having hydroxyalkyl groups which are further reacted with hydroxyalkyl esters of acrylic or methacrylic acid to form compounds with pendant groups having ethylenic unsaturation positioned α,β from a carbonyl group (referred to herein as "α,β-unsaturated carbonyl groups"). In the presence of a suitable initiator, the unsaturated aminoplasts can be cured by either thermal or irradiative means (or a combination thereof) to form a hard, crosslinked binder resin which finds utility in abrasive articles. Many compounds previously used as diluents, such as the alkoxylated polyacrylates, are not effective solvents for aminoplast resins.

Thus, there is a need for reactive diluents which exhibit excellent solubility for aminoplast resins, which are highly reactive to both photochemical and thermal free-radical polymerization, which exhibit low vapor pressures, which exhibit low viscosity at temperatures of about 20° C. and which enhance or, at the least, do not diminish, the hardness of cured resins in which they are used. We have discovered several such diluents.

SUMMARY OF THE INVENTION

The compounds and compositions of the present invention overcome or reduce many of the aforementioned problems associated with previously known coatable, radiation curable binder precursor compositions. In accordance with the present invention, compounds which are suitable as reactive diluents in addition polymerizable binder precursor compositions are presented which exhibit excellent solubility for aminoplast resins, which are highly reactive to both photochemical and thermal free radical polymerization, which exhibit low vapor pressures, which exhibit low viscosity at temperatures of about 20° C. and which enhance or, at least, do not diminish, the hardness of cured binder resins into which they are reacted.

Compounds of the invention suitable for use as reactive diluents include the compounds selected from the group consisting of:

(a) compounds selected from the group consisting of compounds within general formula (I):

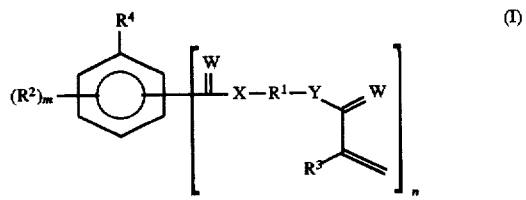

wherein:

$R^1$ is an organic radical having from 1 to 12 carbon atoms;

$R^2$ is selected from the group consisting of:
i) organic radicals devoid of reactive groups other than optional ethylenically-unsaturated groups and selected from the group consisting of organic radicals having from 1 to 12 carbon atoms, and ii) moieties which do not substantially terminate polymerization of ethylenically-unsaturated groups;

$R^3$ is H;

$R^4$ is selected from the group consisting of H, —OH, —O—C(=O)—C($R^5$)=CH$_2$, and —NR$^6$—C(=O)—C($R^5$)=CH$_2$; preferably, $R^4$ is selected from the group consisting of —OH, —O—C(=O)—CH=CH$_2$, and —NR$^6$—C(=O)—CH=CH$_2$; more preferably, $R^4$ is selected from the group consisting of —OH and —O—C(=O)—CH=CH$_2$;

$R^5$ is selected from the group consisting of H and organic radicals having 1 to 12 carbon atoms;

$R^6$ is selected from the group consisting of H, alkyl groups having 1 to 12 carbon atoms, —C(=O)—CH=CH$_2$, and —R$^1$—O—C(=O)—CH=CH$_2$;

W is selected from the group consisting of O, S, NR$^5$; X and Y are independently selected from the group consisting of O, S, NR$^6$, with the proviso that all W, X and Y groups cannot be O;

m is an integer ranging from 0 to 2; and n is 1 or 2, with the proviso that when n=1, $R^4$ is not H;

(b) aromatic compounds selected from the group consisting of compounds within general formula (II):

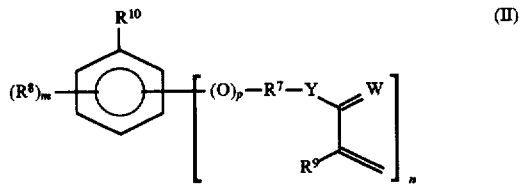

wherein:

$R^7$ is an organic radical having from 1 to 12 carbon atoms;

$R^8$ is selected from the group consisting of:

i) organic radicals devoid of reactive groups other than optional ethylenically-unsaturated groups and selected from the group consisting of organic radicals having from 1 to 12 carbon atoms, and ii) moieties which do not substantially terminate polymerization of ethylenically-unsaturated groups;

$R^9$ is H or an organic radical having 1 to 12 carbon atoms;

$R^{10}$ is selected from the group consisting of —OH, —O—C(=O)—C(R$^9$)=CH$_2$, and —NR$^{11}$—C(=O)—C(R$^9$)=CH$_2$; preferably, $R^{10}$ is selected from the group consisting of —OH, —O—C(=O)—CH=CH$_2$, and —NR$^{11}$—C(=O)—CH=CH$_2$; more preferably, $R^{10}$ is selected from the group consisting of —OH and —O—(=O)—C(H)=CH$_2$;

$R^{11}$ is selected from the group consisting of H, organic radicals having 1 to 12 carbon atoms, —C(=O)—C (R$^9$)=CH$_2$, and —R$^7$—O—C(=O)—C—(R$^9$)=CH$_2$;

W is selected from the group consisting of O, S, NR$^9$; Y is selected from the group consisting of O, S, NR$^{11}$;

m is an integer ranging from 0 to 2;

n is 1 or 2; and p is 0 or 1, with the proviso that when p=0 and $R^7$ is —CH$_2$—, Y cannot be NR$^{11}$;

(c) N-substituted succinimide derivatives selected from the group consisting of compounds within general formula (III):

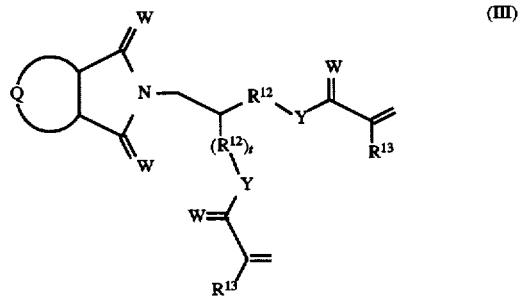

wherein:

$R^{12}$ is an organic radical having from 1 to 12 carbon atoms;

$R^{13}$ is H or an organic radical having 1 to 12 carbon atoms;

W is selected from the group consisting of O, S, NR$^{13}$; Y is selected from the group consisting of O, S, NR$^4$;

$R^{14}$ is selected from the group consisting of H, organic radicals having 1 to 12 carbon atoms, —C(=O)—C (R$^{13}$)=CH$_2$, and —R$^2$—O—C(=O)—C(R$^3$)=CH$_2$;

n is 1 or 2;

Q is an organic radical, such that fused cycloaliphatic, bicycloaliphatic, and aromatic rings are formed with bridgehead carbons at positions 3 and 4 of the N-substituted succinimide ring, wherein Q is devoid of ring substituents which substantially interfere with free radical polymerization of ethylenically unsaturated groups; Q preferably has from 0 to 3 —C=C— linkages; in addition, the organic radical representing Q preferably has 1 to 10 carbon atoms; more preferably, Q is selected to form phthalimide, hexahydrophthalimide, tetrahydrophthalimide, and derivatives thereof with the N-substituted succinimide ring;

t is 0 or 1;

(d) heterocyclic compounds selected from the group consisting of compounds within general formula (IV):

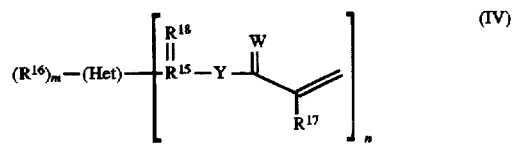

wherein:

$R^5$ is an organic radical having from 1 to 12 carbon atoms;

$R^{16}$ is selected from the group consisting of:

i) organic radicals devoid of reactive groups other than optional ethylenically-unsaturated groups and selected from the group consisting of organic radicals having from 1 to 12 carbon atoms, and ii) moieties which do not substantially terminate polymerization of ethylenically-unsaturated groups;

$R^{17}$ is H or an organic radical having 1 to 12 carbon atoms;

$R^{18}$ is selected from the group consisting of H, —(R$^{15}$),—O—C(=O)—C(R$^{17}$)=CH$_2$, and —(R$^{15}$),—N(R$^{19}$)—C(=O)—C(R$^{17}$)=CH$_2$; preferably, $R^{18}$ is H;

$R^{19}$ is selected from the group consisting of H, organic radicals having 1 to 12 carbon atoms, —C(=O)—C (R$^{17}$)=CH$_2$, and —R$^{15}$—O—C(=O)—C(R$^{17}$)=CH$_2$;

W is selected from the group consisting of O, S, NR$^{17}$; Y is selected from the group consisting of O, S, NR$^{19}$;

m is an integer ranging from 0 to 2;

n is 1 or 2;

t is 0 or 1; and

Het is a cyclic organic radical having at least one ring heteroatom, i.e., at least one heteroatom in the ring; Het being selected from the group consisting of thiazole, oxazole, pyrrole, N-acryloylpiperazine, N-acryloylpiperidine; preferably, Het is selected from the group consisting of thiazole, N-acryloylpiperazine, and N-acryloylpiperidine; and (e) heterocyclic compounds selected from the group consisting of compounds within general formula (V):

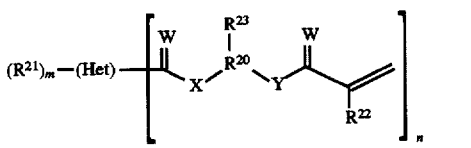

(V)

wherein:

$R^{20}$ is an organic radical having from 1 to 12 carbon atoms;

$R^{21}$ is selected from the group consisting of:
i) organic radicals devoid of reactive groups other than optional ethylenically-unsaturated groups and selected from the group consisting of organic radicals having from 1 to 12 carbon atoms, and ii) moieties which do not substantially terminate polymerization of ethylenically-unsaturated groups;

$R^{22}$ is H or an organic radical having 1 to 12 carbon atoms;

$R^{23}$ is selected from the group consisting of —H, —($R^{20}$)$_t$—O—C(=O)—C($R^{22}$)=CH$_2$, and —($R^{20}$)$_t$—N($R^{24}$)—C(=O)—C($R^{22}$)=CH$_2$; preferably, $R^{23}$ is H;

$R^{24}$ is selected from the group consisting of H, organic radicals having 1 to 12 carbon atoms, —C(=O)—C($R^{22}$)=CH$_2$; and —$R^{20}$—O—C(=O)—C—($R^{22}$)=CH$_2$;

W is selected from the group consisting of O, S, $NR^{22}$; X and Y are independently selected from the group consisting of O, S, $NR^{24}$;

m is an integer ranging from 0 to 2;

n is 1 or 2;

t is 0 or 1; and

Het is a cyclic organic radical having at least one ring heteroatom, i.e., at least one heteroatom in the ring; Het being selected from the group consisting of imidazole, thiazole, oxazole, pyrrole, N-acryloylpiperazine, N-acryloylpiperidine, thiophene, and furan, with the proviso that when all W, X, and Y groups are O and n=1, Het cannot be furan. Preferably, Het is selected from the group consisting of thiophene and furan.

Another aspect of the invention is a coatable, curable binder precursor composition comprising an addition polymerizable resin and at least one of the above-mentioned inventive reactive diluent compounds, and optionally an inert diluent liquid. The inventive compounds preferably comprise from about 1 to about 80 weight percent of the inventive compositions, more preferably from about 10 to about 70 weight percent, particularly from about 20 to about 60 weight percent, based on total weight of said compositions.

Compositions within the invention cure to hardened binders having a Knoop Hardness Number preferably ranging from about 20 to about 50.

The term "coatable", as used herein, means that the binder precursor compositions of the invention may be easily coated or sprayed onto substrates using conventional coating devices, such as knife coaters, roll coaters, flow-bar coaters, spray coaters, die coaters (including vacuum die coaters), and the like. This characteristic may also be expressed in terms of viscosity of the compositions. The viscosity of the inventive coatable, radiation curable binder precursor compositions should not exceed about 2000 centipoise (cps), measured using a Brookfield viscometer, No. 2 spindle, 60 rpm, at 25° C.

The term "reactive" when used in the context "reactive diluent" means that the compound has moieties allowing it to be reacted with the other resin components, for example, acrylate moieties.

The term "diluent" is used in the sense that the inventive reactive diluent compounds (and optional inert diluent liquids) dilute the concentration of radiation curable resin in the compositions of the invention, and does not mean that the composition is necessarily decreased in viscosity, although viscosity reduction is preferred.

The term "polar" as used herein has its generally accepted meaning and means the functional group exhibits an increased electronegativity relative to surrounding atoms, and, in particular, relative to adjacent carbon atoms. A polar group preferably includes one or more heteroatoms such as N (nitrogen) and O (oxygen).

The addition polymerizable resin is preferably a radiation-curable aminoplast resin. Particularly preferred radiation-curable aminoplast resins are those described in U.S. Pat Nos. 4,903,440, 5,055,113, and 5,236,472, the radiation-curable aminoplast resin disclosures of which are incorporated herein by reference.

Another aspect of the invention is a coatable binder precursor composition having from about 40 to about 99 weight percent addition polymerizable monomers, and from about 1 to about 60 weight percent of thermal condensation curable monomers and oligomers, based on the total weight of polymerizable monomers. Thus, conventional thermal condensation curable resins such as phenol-formaldehyde, urea-formaldehyde, melamine-formaldehyde, and furfural resins can be admixed with the addition polymerizable resins. Further aspects and advantages of the invention will become apparent from the description of preferred embodiments which follows.

DESCRIPTION OF PREFERRED EMBODIMENTS

Reactive Diluents

The inventive compounds functional as reactive diluents and therefore useful in the production of abrasive and other articles are preferably made by a generic process which is detailed in the examples for each particular compound. As explained further herein below, the compounds of the invention facilitate solubilization of polar resins, and generally have an effect on the cured compositions. In general, the compounds of the invention function to increase the glass transition temperature of cured compositions in which they are employed. This in turn translates into a more thermally stable cured composition, which can be important in some applications, such as when the inventive compositions are used to form coated abrasive articles. The effect of adding the inventive compounds to compositions on the properties of cured compositions may be determined by dynamic mechanical analysis, as further discussed below.

Compounds within the invention suitable for use as reactive diluents comprise one or two organic linking radicals (in the case of compounds within general formulas (I), (II), (IV) and (V) when n is 1 or 2) or only one organic linking radical (compounds within general formula (III)) which links the ethylenically-unsaturated group(s) to a polar organic moiety. The linking radicals may include as part of their structure either one or two organic radicals having 1 to 12 carbon atoms, depending on the particular compound.

In general formulas (I) to (V), $R^1$, $R^7$, $R^{12}$, $R^{15}$, and $R^{20}$, respectively and independently, are selected from the group consisting of organic radicals having from 1 to 12 carbon atoms. Preferably, $R^1$, $R^7$, $R^{12}$, $R^{15}$, and $R^{20}$ are independently selected from the group consisting of —$C_xH_{2x}$— and —$(C_yH_{2y})$—O—$(C_yH_{2y'})$— wherein x is an integer ranging from 1 to 12 (inclusive) and y and y' are independently selected from integers ranging from 1 to 6 (inclusive). More preferably, $R^1$, $R^7$, $R^{12}$, $R^{15}$, and $R^{20}$, respectively and independently, are selected from the group consisting of —$CH_2$—, —$CH_2$—$CH_2$—, —$CH_2$—$CH_2$—$CH_2$—, and —$CH_2$—$CH_2$—O—$CH_2$—$CH_2$—. In general formulas (I) to (V) having more than one $R^1$, $R^7$, $R^{12}$, $R^{15}$, or $R^{20}$, respectively; $R^1$, $R^7$, $R^{12}$, $R^{15}$, and $R^{20}$, respectively, are independently selected and may be the same or different. The constitution of $R^1$, $R^7$, $R^{12}$, $R^{15}$, and $R^{20}$ in each molecule of the inventive reactive diluents are not particularly limited (within the viscosity limitations discussed herein). Notably, $R^1$, $R^7$, and $R^{12}$, respectfully are di-substituted and $R^{15}$ and $R^{20}$, respectively, can be di- or tri-substituted.

Compounds of the invention comprise at least one polar functional group or moiety. The polar moieties are as follows: in general formula (I), the aromatic —C=W moiety; in general formula (II), the aromatic ring having pendant $R^8$ and $R^{10}$; in general formula (III), the succinimide moiety including W and Q; in general formula (IV), the $(R^{16})_m$-(Het) moiety; and in general formula (V), the $(R^{21})_m$-(Het) moiety.

The polar functional group or moiety facilitates the solubilization of polar resins, such as aminoplast resins, in the inventive reactive diluents. The term "polar" as used herein has its generally accepted meaning and means the functional group exhibits an increased electropositivity or electronegativity relative to surrounding atoms, and, in particular, relative to adjacent carbon atoms.

In compounds within general formulas (I), (II), (IV), and (V) herein, $R^2$, $R^8$, $R^{16}$, and $R^{21}$, respectively and independently, are selected from the group consisting of organic radicals devoid of reactive groups other than optional ethylenically-unsaturated groups and selected from the group consisting of radicals having from 1 to 12 carbon atoms; and moieties which do not substantially terminate polymerization of ethylenically-unsaturated groups.

In general formulas (I), (II), (IV), and (V), when m is 2, the $R^2$ groups in general formula (I), the $R^8$ groups in general formula (II), the $R^{16}$ groups in general formula (IV), and the $R^{21}$ groups in general formula (V), respectively and independently, preferably form a fused organic ring structure, e.g., fused aromatic, fused cycloaliphatic, fused bicycloaromatic, and fused heterocyclic rings, which can be hydrogenated or partially hydrogenated and can be substituted with one or more groups, e.g., amino, halo, alkoxy, and carboxyl. Preferably, the fused organic ring structures are fused aromatic (e.g., substituted monocyclic aromatic rings), fused cycloaliphatic (e.g., fused monocyclic aliphatic rings), fused bicycloaromatic, and fused heterocyclic rings (e.g., pyrrole, furan, thiophene, imidazole, pyrazole, thiazole, oxazole) having from 1 to about 7 ring atoms. The terms "cycloaliphatic" and "bicycloaliphatic" as used herein are meant to include ring structures having 3 to 10 and 3 to 20 carbon atoms, respectively, and which may have some degree of unsaturation, for example a $C_5$ ring may have one —C=C— linkage.

$R^2$, $R^8$, $R^{16}$, and $R^{21}$, respectively and independently, are also preferably selected from the group consisting of amino, halo, alkoxy and carboxyl, with the proviso that such groups are selected so that they do not interfere with subsequent free-radical polymerization of the inventive compound(s).

In general formulas (II), (III), (IV), (V); $R^9$, $R^{13}$, $R^{17}$, and $R^{22}$, respectively and independently, are H or an organic radical having 1 to 12 carbon atoms. Preferably, $R^9$, $R^{13}$, $R^{17}$, and $R^{22}$, respectively and independently, are H.

Sometimes there is no clear distinction between the polar group or moiety and the linking group of the inventive compounds, these categorizations being merely used for convenience. For example, the linking portion of useful compounds within the invention may have polar moieties. For example, polar moieties are formed when W is O in general formula (III), thus forming cyclic imides.

The W groups in formulas (I) to (V), respectively, preferably are independently O or NT' wherein T' is H or an organic radical having 1 to 12 carbon atoms. The X and Y groups (where present) in formulas (I) to (V), respectively, preferably are independently O or NT'' wherein T'' is H, organic radicals having 1 to 12 carbon atoms, —C(=O)—C(T')=$CH_2$, and —(T'')—O—C(=O)—C(T')=$CH_2$. T' represents the "R" substituents in general formulas (I) to (V) which are defined as H or an organic radical having 1 to 12 carbon atoms and which are described as being attached to the nitrogen-containing group which can be representative of W (for example, $R^5$ in general formula (I), $R^9$ in general formula (II), $R^{13}$ in general formula (III), $R^{17}$ in general formula (IV), $R^{22}$ in general formula (V)). T'' represents the "R" substituents in general formulas (I) to (V) which are defined as H, organic radicals having 1 to 12 carbon atoms, —C(=O)—C(T')=$CH_2$, and —(T''')—O—C(=O)—C(T') =$CH_2$ (T''' is an organic radical having 1 to 12 carbon atoms) and which are described as being attached to the nitrogen-containing group which can be representative of X and Y (for example, $R^6$ in general formula (I), $R^{11}$ in general formula (II), $R^{14}$ in general formula (III), $R^{19}$ in general formula (IV), $R^{24}$ in general formula (V)). Preferably, T'' is selected from the group consisting of H, $C_xH_{2x+1}$, —C(=O)C(T')=$CH_2$, and —$C_xH_{2x}$—O—C(=O)—C(T')=$CH_2$, wherein x is an integer ranging from 1 to 12 (inclusive) and T' is as defined above. As stated above, however, in general formula (I), all W, X, and Y cannot be O and, in general formula (V), when W, X, and Y are O and n=1, Het cannot be furan.

The inventive compounds comprise at least one ethylenically-unsaturated group which copolymerizes or crosslinks with ethylenically-unsaturated groups present in the addition polymerizable resin. Although there is no particular upper limitation on the number of ethylenically-unsaturated groups in each molecule of the inventive compounds (other than viscosity limitations discussed herein), up to and including 10 ethylenically-unsaturated groups may be present in the inventive compounds, preferably from 1 to 4, and most preferably either 1 or 2 ethylenically-unsaturated groups are present in each reactive diluent molecule.

The non-optional ethylenically-unsaturated group(s) of the inventive reactive diluent compounds are preferably selected from the group consisting of acryloyl, methacryloyl, thioacryloyl, thiomethacryloyl, N-substituted acrylamidoyl and N-substituted methacrylamidoyl and are more preferably selected from the group consisting of acryloyl and N-substituted acrylamidoyl.

Particularly preferred reactive diluent compounds are those within general formulas (I), (IV), and (V), wherein W is O and X and Y are selected from O and N(T''), thus forming —C(=O)O— and —C(=O)N(T'')— groups, respectively. T'' is as defined above. As stated above, however, in general formula (I), all W, X, and Y cannot be O and in general formula (V), when W, X, and Y are O and n=1, Het cannot be furan.

Other particularly preferred reactive diluents are those within general formula (III) when a cyclic imide is fused to a group selected from a carbocyclic ring (i.e., phthalimide), because polar functional groups provide sufficient solubility of resins in the reactive diluent, are easily prepared, and are thermally stable. Particularly preferred compounds of the invention useful as reactive diluents are selected from the group consisting of:

(i) cyclic imides within general formula (VI):

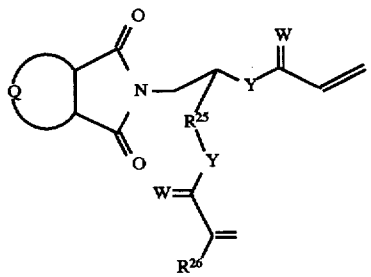

(VI)

wherein:

Q is an organic radical, such that fused cycloaliphatic, bicycloaliphatic, and aromatic rings are formed with bridgehead carbons at positions 3 and 4 of the N-substituted succinimide ring, wherein Q is devoid of ring substituents which substantially interfere with free radical polymerization of ethylenically unsaturated groups; Q preferably has from 0 to 3 —C=C— linkages; in addition, the organic radical representing Q preferably has 1 to 10 carbon atoms; more preferably, Q is selected to form phthalimide, hexahydrophthalimide, tetrahydrophthalimide, and derivatives thereof with the N-substituted succinimide ring;

W is selected from the group consisting of $NR^{27}$, O, and S;

Y is selected from the group consisting of O, S, and $NR^{28}$;

$R^{25}$ is an organic radical having from 1 to 12 carbon atoms;

$R^{26}$ is selected from the group consisting of —H and organic radicals having from 1 to 12 carbon atoms;

$R^{27}$ is selected from the group consisting of H and $—C_xH_{2x+1}$;

$R^{28}$ is selected from the group consisting of H, $—C_xH_{2x+1}$, $—C(=W)—CH=CH_2$, and $C_xH_{2x}—O—C(=W)—CH=CH_2$; and x ranges from 1 to 10 inclusive;

$R^{27}$ and $R^{28}$ may be the same or different;

(ii) compounds within general formula (VII):

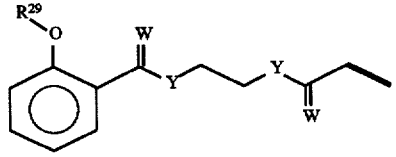

(VII)

wherein:

each W is independently selected from the group consisting of $NR^{30}$, O, and S;

each Y is selected independently and can be the same or different, Y being selected from the group consisting of O, S, and $NR^{31}$, with the proviso that all W and Y groups cannot be O;

$R^{29}$ is selected from the group consisting of H and $—C(=W)—CH=CH_2$;

$R^{30}$ is selected from the group consisting of H and $—C_xH_{2x+1}$;

$R^{31}$ is selected from the group consisting of H, $—C_xH_{2x+1}$, $—C(=W)—CH=CH_2$, and $C_xH_{2x}—O—C(=W)—CH=CH_2$; and x ranges from 1 to 10 inclusive;

$R^{30}$ and $R^{31}$ may be the same or different;

(iii) compounds within general formula (VIII):

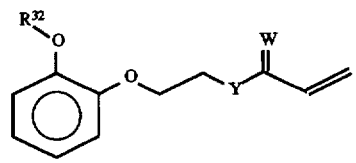

(VIII)

wherein:

W is selected from the group consisting of $NR^{33}$, O, and S;

Y is selected from the group consisting of O, S, and $NR^{34}$;

$R^{32}$ is selected from the group consisting of H and $—C(=W)—CH=CH_2$;

$R^{33}$ is selected from the group consisting of H and $—C_xH_{2x+1}$;

$R^{34}$ is selected from the group consisting of H, $—C_xH_{2x+1}$, $—C(=W)—CH=CH_2$, and $—C_xH_{2x}—O—C(=W)—CH=CH_2$; and x ranges from 1 to 10 inclusive;

$R^{33}$ and $R^{34}$ may be the same or different;

(iv) aromatic compounds within general formula

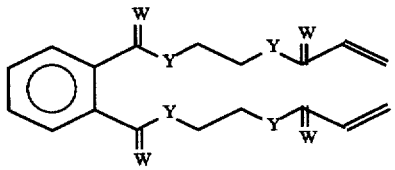

(IX)

wherein:

each W is independently selected from the group consisting of $NR^{35}$, O, and S;

each Y is independently selected from the group consisting of O, S, and $NR^{36}$, with the proviso that all W and Y groups cannot be O;

$R^{35}$ is selected from the group consisting of H and $—C_xH_{2x+1}$;

$R^{36}$ is selected from the group consisting of H, $—C_xH_{2x+1}$, $—C(=W)—CH=CH_2$, $—C_xH_{2x}—O—C(=W)—CH=CH_2$; and x ranges from 1 to 10 inclusive;

$R^{35}$ and $R^{36}$ may be the same or different;

(v) heterocyclic compounds within general formula (X):

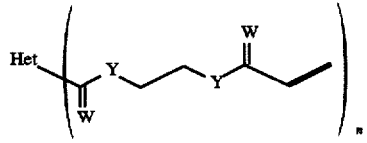

(X)

wherein:

each W is independently selected from the group consisting of $NR^{37}$, O, and S;

each Y is independently selected from the group consisting of O, S, and NR$^{38}$;

R$^{37}$ is selected from the group consisting of H and —C$_x$H$_{2x+1}$;

R$^{38}$ is selected from the group consisting of H, —C$_x$H$_{2x+1}$, —C(=W)—CH=CH$_2$, and —C$_x$H$_{2x}$—O—C(=W)—CH=CH$_2$;

Het is a heterocyclic ring selected from the group consisting of furan, thiophene, thiazole, oxazole, imidazole, and oxazoline, with the proviso that when all W and Y groups are O and n=1, Het cannot be furan;

n is an integer ranging from 1 to about 4; and x ranges from 1 to 10 inclusive;

R$^{37}$ and R$^{38}$ may be the same or different; and (vi) heterocyclic compounds within general formula (XI):

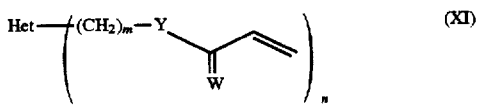

(XI)

wherein:

each W is independently selected from the group consisting of NR$^{39}$, O, and S;

each Y is independently selected from the group consisting of O, S, and NR$^{40}$;

R$^{39}$ is selected from the group consisting of H and —C$_x$H$_{2x+1}$;

R$^{40}$ is selected from the group consisting of H, —C$_x$H$_{2x+1}$, —C(=W)—CH=CH$_2$, —C$_x$H$_{2x}$—O—C(=W)—CH=CH$_2$;

Het is a heterocyclic ring selected from the group consisting of thiazole, oxazole, N-acryloylpiperidine, and N-acryloylpiperazine;

m=1 or 2;

n is an integer ranging from 1 to about 4; and x ranges from 1 to 10 inclusive;

R$^{39}$ and R$^4$ may be the same or different.

Other preferred compounds useful as reactive diluents and within the invention are selected from the group consisting of:

(vii) carbocyclic imides within general formula (XII):

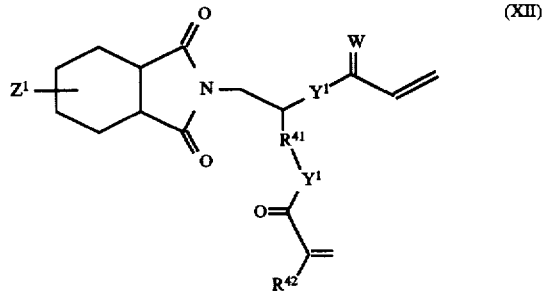

(XII)

wherein:

Z$^1$ is selected from the group consisting of H, and —C$_x$H$_{2x+1}$ wherein x ranges from 1 to 10 inclusive;

Y$^1$ is selected from the group consisting of NR$^{43}$ and O;

W is selected from the group consisting of O, S NR$^{42}$;

R$^{41}$ is an organic radical having from 1 to 12 carbon atoms;

R$^{42}$ is selected from the group consisting of —H and organic radicals having from 1 to 12 carbon atoms;

R$^{43}$ is selected from the group consisting of —H, —C$_x$H$_{2x+1}$, —C(=W)—CH=CH$_2$, and —C$_x$H$_{2x}$—O—C(=W)—CH=CH$_2$; and x ranges from 1 to 10 inclusive;

(viii) salicylic acid derivatives within general formula (XIII):

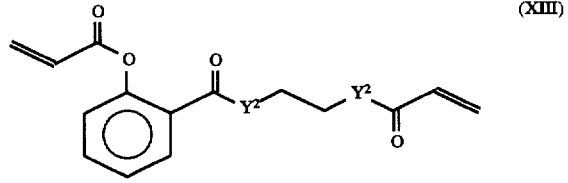

(XIII)

wherein:

each Y$^2$ is independently selected from the group consisting of NR$^{44}$ and O; and R$^{44}$ is selected from the group consisting of —H, —C$_x$H$_{2x+1}$, —C(=O)—CH=CH$_2$, and —C$_x$H$_{2x}$—O—C(=O)—CH=CH$_2$; and x ranges from 1 to 10 inclusive;

(ix) catechol derivatives within general formula (XIV):

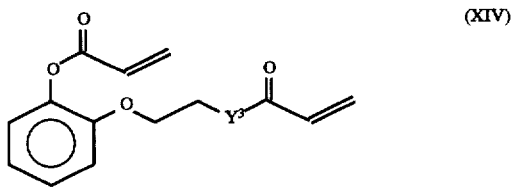

(XIV)

wherein:

Y$^3$ is selected from the group consisting of NR$^{45}$ and O; and

R$^{45}$ is selected from the group consisting of —H, —C$_x$H$_{2x+1}$, —C(=O)—CH=CH$_2$, and —C$_x$H$_{2x}$—O—C(=O)—CH=CH$_2$; and x ranges from 1 to 10 inclusive;

(x) phthalate esters and phthalamides within general formula (XV):

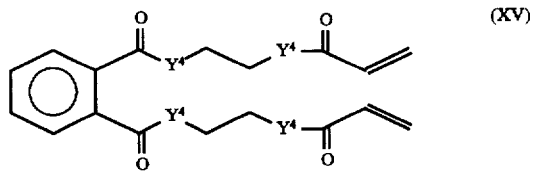

(XV)

wherein:

each Y$^4$ is independently selected from the group consisting of NR$^{46}$ and O, with the proviso that all Y$^4$ groups cannot be O; and R$^{46}$ is selected from the group consisting of —H, —C$_x$H$_{2x+1}$, —C(=O)—C=CH$_2$, and —C$_x$H$_{2x}$—O—C(=O)—CH=CH$_2$;

x ranges from 1 to 10 inclusive;

(xi) heterocyclic acid esters or heterocyclic acid amides within general formula (XVI):

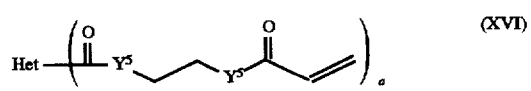

(XVI)

wherein:

each Y$^5$ is independently selected from the group consisting of NR$^{47}$ and O;

$R^{47}$ is selected from the group consisting of —H, —$C_xH_{2x+1}$, —C(=O)—C=$CH_2$, and —$CH_xH_{2x}$—O—C(=O)—C=$CH_2$;

a is 1 or 2;

Het is selected from the group consisting of furanyl, thienyl, 4-alkyl-5-thiazinyl, and imidazolyl, with the proviso that if both $Y^5$ groups are O and a is 1, Het cannot be furan; and x ranges from 1 to 10 inclusive; and (xii) heterocyclic acrylates and heterocyclic acrylamides within general formula (XVII):

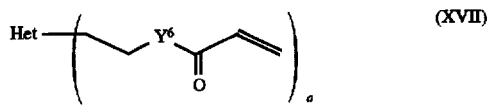

(XVII)

wherein:

each $Y^6$ is independently selected from the group consisting of $NR^{48}$ and O;

$R^{48}$ is selected from the group consisting of —H, —$C_xH_{2x+1}$, —C(=O)—C=$CH_2$, and —$C_xH_{2x}$—O—C(=O)—CH=$CH_2$;

a is 1 or 2;

Het is selected from the group consisting of 4-alkyl-5-thiazinyl, oxazolidin-2-on-5-yl, N-acryloylpiperidine, and N-acryloylpiperazine; and x ranges from 1 to 10 inclusive.

Specific preferred inventive compounds useful as reactive diluents, individually or in combination, include:

N,N'-Di(acryloyloxyethyl)-N,N'-dimethyl phthalamide
N N'-Di(acryloyloxyethyl)-N,N'-diethyl phthalamide
N,N'-Di(acryloyloxyethyl)-N,N'-dipropyl phthalamide
2,6-Di(acryloyloxymethyl)-p-cresol acrylate
2-(Acryloyloxyethoxy)phenol
2-(Acryloyloxyethoxy)phenol acrylate
N-[2,3-Di(acryloyloxy)propyl]tetrahydrophthalimide
N-[2,3-Di(acryloyloxy)propyl]hexahydrophthalimide
N-[2,3-Di(acryloyloxy)propyl]methyl nadimide
5-(Acryloyloxyethyl)-4-methylthiazole
N-(2-Acryloyloxyethyl)-N'-(acryloyl)piperazine
2-(2-Acryloyloxyethyl)-N-(acryloyl)piperidine
2-(Acryloyloxyethyl)thenoate
2-[N-(Acryloyloxyethyl)-N-methyl]thiophenecarboxamide
2-[N-(Acryloyloxyethyl)-N-ethyl]thiophenecarboxamide
2-[N-(Acryloyloxyethyl)-N-propyl]thiophenecarboxamide
2-[N,N-Di(acryloyloxethyl)]thiophenecarboxamide
2-[N-(Acryloyloxyethyl)]-N-methyl]furancarboxamide
2-[N,N-Di(acryloyloxyethyl)]furancarboxamide.

Methods of production of compounds within the invention are presented in the Examples section.

Solvent Power

Compounds within the invention useful as reactive diluents exhibit particularly excellent solvency towards radiation curable aminoplast resins having α,β-unsaturated carbonyl groups such as those described in U.S. Pat. Nos. 4,903,440 (the '440 patent), 5,055,113 (the '113 patent), and 5,236,472 (the '472 patent), all assigned to the assignee of the present application. The inventive compounds also exhibit excellent solvency toward phenolic resins, urethane resins, oligoacrylate resins and epoxy resins. Among these resins, the aminoplast resins are known to be quite insoluble in most known acrylate-functional reactive diluents.

Specifically, a compound useful as a reactive diluent preferably dissolves at least its own weight of acrylamidomethylated phenol (hereinafter referred to as "AMP") described in the '440 patent, or acrylamidomethyl novolak resin (hereinafter referred to as "AMN") described in the '472 patent. Thus, as an example, at least 10 grams of acrylamidomethyl phenol preferably dissolves completely in 10 grams of an inventive compound at 20° C. in order for the inventive compound to be considered as exhibiting sufficient solvency towards aminoplast resins. More preferably, compounds of the invention dissolve at least 120% of their weight of aminoplast resins, and, most preferably, compounds of the invention dissolve at least 150% of their weight of aminoplast resins, in order for the resulting cured resin formulations to exhibit the required combination of hardness and durability.

Viscosity

In order to be useful in the preparation of cured resin systems, the novel compounds of the invention typically and preferably exhibit viscosities ranging from about 30 centipoise (cps) to about 2000 cps at about 20° C., as measured by a Brookfield viscometer model number LVF, No. 4 spindle, 60 rpm, at 25° C., as described in American Society of Testing and Materials (ASTM) test No. 1824-87. Preferably, compounds within the invention exhibit viscosities ranging from about 30 cps to about 1000 cps at about 20° C., and, most preferably, viscosities ranging from about 30 cps to about 500 cps at about 20° C.

While the viscosity of the inventive reactive diluent compound itself is critical, the viscosity of resin formulations comprising the inventive compounds and resins such as aminoplasts, epoxy resins, and the like, is also critical to the utility of the inventive compounds. Thus, formulations comprising about 50 parts by weight aminoplast resin and about 50 parts by weight reactive diluent(s) preferably exhibit viscosities in the range of from about 30 cps to about 5000 cps, more preferably from about 30 to about 2000, in order to be readily coatable on substrates known in the abrasive materials art using standard coating methods and apparatus known in the abrasive materials art.

Resin Systems

Compounds within the invention useful as reactive diluents are used in conjunction with known resin materials to prepare, e.g., rapidly curable make coatings and size coatings for abrasive constructions. In these applications, a coatable composition comprising the resin dissolved in the inventive reactive diluent, along with optional photoinitiators, thermal initiators, fillers, pigments and other additives known in the art, is prepared and coated onto a substrate. The coating is cured by exposure to energy sufficient to cure the coatings, preferably radiation energy and, optionally, thermal energy.

While conventional thermal condensation curable resins such as phenol-formaldehyde, urea-formaldehyde, melamine and furfural resins can be admixed with the above-described coatable compositions, the preferred resin is a radiation-curable aminoplast resin as described in the above-mentioned '440, '113 and '472 patents, the disclosures of which are incorporated by reference herein for the purpose of disclosure of those resins.

Aminoplast resins, which are also interchangeably referred to as "aminoplasts" herein, are obtained by reacting amino-functional compounds with aldehydes to produce compounds having hydroxyalkyl groups. The most common and preferred aldehyde is formaldehyde, which reacts with the amino group (—NHR) to produce compounds having hydroxymethyl groups. The R substituent of the —NHR group is typically and preferably a hydrogen or a hydrocarbon, which may be substituted or unsubstituted, but, if substituted, the substituent or substituents should be those that do not inhibit or prevent polymerization.

Preferably, aminoplast resins useful as curable abrasive binders have an average of at least 1.1 pendant $\alpha,\beta$-unsaturated carbonyl groups per molecule. The $\alpha,\beta$-unsaturated carbonyl groups include acrylates, methacrylates, acrylamides and methacrylamides, and mixtures thereof. These aminoplast resins polymerize via free-radical polymerization at the site of the $\alpha,\beta$-unsaturated carbonyl groups and are curable by either heat or irradiation.

In addition, the aminoplasts can also contain pendant amino (—NHR) or hydroxyl (—OH) functional groups, where the R substituent is typically and preferably a hydrogen or a hydrocarbon, which may be substituted or unsubstituted, but, if substituted, the substituent or substituents should be those that do not inhibit or prevent polymerization. Preferred examples of the R substituent include alkyl (e.g., methyl, ethyl, and the like), aryl (e.g., phenyl and the like), alkoxy and carbonyl.

Preferably, resin systems for preparing binders for abrasives are selected from the group consisting of:

A. aminoplast resins having on average at least 1.1 pendant $\alpha,\beta$-unsaturated carbonyl groups per molecule, B. aminoplast resins having on average at least 1.1 pendant $\alpha,\beta$-unsaturated carbonyl groups per molecule and at least one pendant —NHR or —OH functional group per molecule, and C. condensation curable resins and aminoplast resins having on average at least 1.1 pendant $\alpha,\beta$-unsaturated carbonyl groups per molecule and at least one pendant —NHR or —OH functional group per molecule.

Most preferably, aminoplast resins used in conjunction with reactive diluents of the invention are selected from the group consisting of acrylamidomethyl phenol, acrylamidomethyl novolak, melamine acrylate resin, bis(acrylamidomethyl ether), tetra(acrylamidomethyl) glycoluril, and N-(hydroxymethyl)acrylamide, and mixtures thereof.

Curing and Cure Rate

The rate at which reactive diluents of the invention cure is an important measure of their utility in resin formulations for abrasive articles. If the reactive diluent cures at a rate significantly slower than the aminoplast resin, the resulting cured formulation may have more than one phase and may be unusable as, e.g., an abrasive binder. In addition, a slow-curing reactive diluent will decrease processing speed, which may unnecessarily increase the cost of the final abrasive product. If the reactive diluent cures at a rate significantly faster than the aminoplast resin, the resulting cured material may be biphasic and may not exhibit the overall hardness required for an abrasive product.

Aminoplast resins are typically and preferably cured by exposure to two ultraviolet lamps operating at 236 watts/cm$^2$ (600 watts/in$^2$) each, operating in the range of 200 to 700 nanometers, preferably 250 to 400 nanometers wavelength, at a web rate ranging from about 3 to about 100 meters/minute. Of course, it is understood that the rate of curing with radiation energy varies according to the binder thickness as well as the density and nature of the composition, and with the intensity of the radiation.

In general, during the manufacture of an abrasive article, such as described in copending patent application Ser. No. 08/144,199, filed on the same day as the present application, a binder precursor composition of the invention is applied to a substrate and cured or polymerized. This polymerization is generally initiated upon exposure to an energy source. Examples of energy sources include thermal energy and radiation energy. The amount of energy depends upon several factors such as the binder precursor chemistry, the thickness of the applied binder precursor coating, the amount and type of particulate matter in the binder precursor, if any, and the amount and type of other optional additives. For thermal curing, temperatures may range from about 30° to about 150° C., more preferably between about 40° and 120° C. The exposure time for thermal curing may range from about 5 minutes to over 24 hours.

Suitable radiation energy sources include electron beam, ultraviolet light and/or visible light. Electron beam radiation, which is also known as ionizing radiation, can be used at an energy level ranging from about 0.1 to about 10 Mrad, preferably at an energy level of about 1 to about 10 Mrads. Ultraviolet radiation refers to non-particulate radiation having a wavelength ranging from about 200 to about 400 nanometers, preferably within the range of about 250 to about 400 nanometers. It is preferred that the ultraviolet light have an intensity of about 300 to about 600 watts/inch. Visible radiation refers to non-particulate radiation having a wavelength within the range of about 400 to about 800 nanometers, preferably in the range of about 400 to about 550 nanometers.

A photoinitiator is preferred to initiate the free-radical polymerization of the addition polymerizable resins and reactive diluent compounds of the invention, either with or without the use of sensitizers. Examples of such photoinitiators are organic peroxides, azo compounds, acyl halides, hydrazones, mercapto compounds, pyrylium compounds, triacylimidazoles, bisimidazoles, chloroalkyltriazines, benzoin ethers, benzyl ketals, thioxanthones, and acetophenone derivatives. Additional references to free-radical photoinitiator systems for ethylenically-unsaturated compounds are described in U.S. Pat. Nos. 3,887,450, 3,895,949, and 3,775,113; and in "Light Sensitive Systems", by J. Kosar, J. Wiley and Sons, Inc. (1965), especially Chapter 5.

Traditionally, abrasive binder systems are cured thermally. Thermal curing typically requires long heating times at elevated temperatures, a process which may add expense to the abrasive and may contribute to environmental pollution when coating solvents are driven off, or may require that additional steps be taken, using additional equipment and resources, to recover evaporated solvent. A major advantage of the use of the inventive compounds as reactive diluents in 100%-radiation cured binder systems is the reduction or elimination of these wasteful and costly processing steps.

Comparative testing of compounds within the invention against thermally-cured binders requires measuring the effect of a post-radiation heating cycle. Thus, compositions comprising the inventive reactive diluents and addition polymerizable resins were cured by ultraviolet radiation and the Knoop hardness of the cured compositions was tested (see below). Then, the radiation-cured samples were heated an additional one hour at 140° C., and any difference in hardness was noted.

Dynamic Mechanical Analysis

Some of the benefits of adding the compounds of the invention to addition polymerizable compositions may be determined through an analytical technique known as "dynamic mechanical analysis" ("DMA"). Specifically, the degree of curing, molecular weight distribution, phase separation, and glass transition temperature ("$T_g$") of cured compositions may be investigated.

In a typical DMA test a sample of composition to be tested is used to saturate a glass fiber cloth, and the composition cured using an ultraviolet lamp. The composite is then placed in tension held by a film-fiber fixture and placed in an analyzing instrument. The sample is typically subjected to a stepwise temperature increase ("temperature sweep"), usually from about 0° C. to about 250° C. At various temperature points, measurements of energy loss and energy storage in the composition are measured to determine the "storage modulus", typically denoted E', which may be plotted versus temperature. In general the storage modulus for a material decreases with temperature. Increases in E' accompany curing reactions and in most cases is not desired. Also measured is another parameter, (E"), which is defined as the loss modulus. The ratio (E"/E'), a unitless parameter typically denoted "tan δ", may also be plotted versus temperature. The maximum point of the tan δ curve (point where the slope is zero), if well defined, takes place at the $T_g$ of the composition. By comparing the analytical results of a blend with the results obtained from a sample of resin only (both samples having a small percentage of photoinitiator added thereto), the increase in $T_g$ may be determined, as well as the molecular weight distribution and degree of phase separation.

For the compounds within the invention, it is preferred that the compound increase $T_g$ of the resin by at least about 10° C., more preferably at least about 50° C. Compounds outside of the invention will typically have a flat, bimodal or other not well defined maximum for tan δ, and thus the $T_g$ will not be well defined. It is preferred that the molecular weight distribution be narrow. If the distribution is wide the tan δ peak will be broad. Compounds within the invention should also prevent or reduce phase separation of the compositions.

Abrasive Particles

The compounds and compositions of the invention may be mixed with abrasive particles to form slurries useful in the manufacture of abrasive articles, such as those described in U.S. Pat. No. 5,152,917. They also may be used in so-called "make" and "size" coatings to produce coated abrasive articles, and in the production of nonwoven abrasive articles. Examples of abrasive particles suitable for use in the present invention include fused aluminum oxide (which includes brown aluminum oxide, heat treated aluminum oxide and white aluminum oxide), ceramic aluminum oxide, green silicon carbide, silicon carbide, chromia, alumina zirconia, diamond, iron oxide, ceria, cubic boron nitride, garnet and combinations thereof.

The absolute particle size of abrasive particles useful in the invention is not critical and may vary widely from about 0.1 micrometer to about 1500 micrometers. The average particle size is preferably between about 0.1 micrometer to 400 micrometers, more preferably between about 0.1 micrometer to about 100 micrometers, and most preferably between about 0.1 micrometer to about 50 micrometers. It is preferred that the abrasive particles have a MOH hardness of at least about 8, more preferably above 9.

The term "abrasive particles" includes individual abrasive grains and also encompasses multiple individual abrasive grains bonded together to form an abrasive agglomerate. Abrasive agglomerates are further described in U.S. Pat. Nos. 4,311,489; 4,652,275 and 4,799,939, all incorporated herein after by reference for their discussion of abrasive grain agglomerates.

The compounds within the invention have uses other than in coatable compositions suitable for production of abrasive articles. For example, the inventive compounds may be utilized as plasticizers, photoresists, and as components of pressure-sensitive adhesives.

TEST METHOD

Knoop Hardness

This indention hardness determination of organic/polymeric coatings is described in ASTM test No. D 1474- 85 (method A), incorporated herein by reference. Binder precursor compositions to be tested were coated onto glass microscope slides at a thickness of approximately 15 mils (about 0.4 millimeters). Subsequently, the binder precursor coatings were dried/cured by an energy source(s) detailed in the various examples. To determine the Knoop hardness ("KHN") values, a 100 gram load was applied to the surface of the dried/cured coating to be tested by means of a pyramidal-shaped diamond having specified face angles, and converting the length measurement of the resulting permanent indentation to the KHN value. Typical KHN values for coatings used in abrasive binders are known to generally range from about 20 to about 50. A hardness tester known under the trade designation "Tukon", model 200, available from Wilson Instruments, Binghampton, N.Y., was used for the KHN testing.

Abbreviations for Reactive Diluents

Di(acryloyloxyethyl)phthalate (DAP)
(Acryloyloxyethyl)salicylate (SEA)
2,6-Di(acryloyloxymethyl)-p-cresol acrylate (CTA)
2-(Acryloyloxyethoxy)phenol acrylate (PPEDA)
N,N'-Di(acryloyloxyethyl)-N,N'-dimethyl phthalamide (DAMP)
N,N'-Di(acryloyloxyethyl)-N,N'-diethyl phthalamide (DAEP)
N,N'-Di(acryloyloxyethyl)-N,N'-dipropyl phthalamide (DAPP)
Acryloyloxyethyl-N-methyl anilide (PMMA)
(Acryloyloxyethyl)benzoate (BEA)
Phenoxyethyl acrylate (PEA) commercial diluent
Benzyl acrylate (BA) commercial diluent
N-(Acryloyloxyethyl)tetrahydrophthalimide (4HPIA)
N-(Acryloyloxyethyl)hexahydrophthalimide (6HPIA)
N-(Acryloyloxyethyl)methylnadimide (MNIA)
N-(Acryloyloxypropyl)hexahydrophthalimide (6HPIPA)
N-(Acryloyloxyethylethoxy)hexahydrophthalimide (6HPIEEA)
N-[2,3-Di(acryloyloxy)propyl]tetrahydrophthalimide (4HPIDA)
N-[2,3-Di(acryloyloxy)propyl]hexahydrophthalimide (6HPIDA)
N-(Acryloyloxyethyl)pyrrolidone (PYA)
5-Acryloyloxymethyl-oxazolidin-2-one (OXA)
5-(Acryloyloxethyl)-4-methylthiazole (MTA)
2-(Acryloyloxyethyl)furoate (FEA)
2-[N-(Acryloyloxyethyl)-N-methyl]furancarboxamide (FAEA)
2-(Acryloyloxyethyl)thenoate (ThEA)
2-[N-(Acryloyloxyethyl)-N-methyl]thiophenecarboxamide (ThMAA)
2-[N-(Acryloyloxyethyl)-N-ethyl]thiophenecarboxamide (ThEAA)
2-[N-(Acryloyloxyethyl)-N-propyl]thiophenecarboxamide (ThPAA)
2-[N,N-Di(acryloyloxyethyl)]thiophenecarboxamide (ThDEAA)
5,5-Di(acryloyloxymethyl)-2-oxazolidinone (OXDA)
3-Di(acryloyloxymethyl)-2-oxazolidinone (OXE)
(2-Oxo-1,3-dioxolan-4-yl)methyl acrylate (GCA)
2-[N,N-Di(acryloyloxyethyl)]furancarboxamide (FDEAA)
N-2-(Acryloyloxyethyl)morpholine (AMA)
N-(2-Acryloyloxethyl)-N'-(acryloyl)piperazine (PEAA)
N-Acryloylmorpholine (AMORPH)
N-(2-Acryloyloxyethyl)ethyleneurea (RDUA)
5-(Acryloyloxymethyl)-2,2-dimethyldioxolane (KDM)
(2-Ethyl-2-methyl-1,3-dioxolan-4-yl)methyl acrylate (KEM)

5-(Acryloyloxymethyl)-2,2-cyclopentyldioxolane (KCP)
5-(Acryloyloxymethyl)-2,2-dimethyl-5-ethyl-1,3-dioxane (KDME)
5-(Acryloyloxymethyl)-2-ethyl-2-methyl-5-ethyl-1,3-dioxane (KEEM)
2-(2-Acryloyloxyethyl)-N-(acryloyl)piperidine (AAP)

EXAMPLES

The following non-limiting examples will further illustrate the reactive diluents and binder precursor compositions of the present invention. All parts and percentages are based upon weight, unless otherwise specified. "ASTM" refers to American Society of Testing and Materials; "IR" refers to the well known infrared spectroscopy analytical method; "$^{13}$C NMR" refers to the well known carbon 13 nuclear magnetic resonance analytical method; "g" refers to gram (s); "ml" refers to milliliter(s); "mol." refers to mole(s); and "mmHg" refers to millimeters mercury.

Example 1

2,6-Di(acryloyloxymethyl)-p-cresol acrylate (CTA)

A two liter, three necked flask was equipped with an overhead stirrer, nitrogen atmosphere and an addition funnel. Next, the flask was charged with 100 g of 2,6-bis (hydroxymethyl)-p-cresol (0.59 mol.), 800 ml of tetrahydrofuran, 180 g of triethylamine (1.78 mol.) 1.2 g of 4-dimethylaminopyridine and 1 g of phenothiazine. The reaction was cooled with an ice bath and 161 g of acryloyl chloride (1.78 mol.) was added slowly over 1.5 hours. Next, the reaction was warmed to room temperature and stirred for 3 hours. The triethylamine hydrochloride salt was removed by filtration. The remaining mother liquor was evaporated with a rotoevaporator to yield a light brown liquid. The liquid was dissolved in ethyl acetate and washed with HCl(10%), NaCl(aq.), NH$_4$OH(10%), NaCl(aq.) and dried over MgSO$_4$. The ethyl acetate was removed with a rotoevaporator to yield 85 g (44%) of a water white liquid. The liquid became a white semi-solid upon standing. The product was confirmed by IR and $^{13}$C NMR.

Example 2

2-(Acryloyloxyethoxy)phenol acrylate (PPEDA)

A 500-ml, two necked flask was equipped with magnetic stirring bar, nitrogen atmosphere and an addition funnel. The flask was charged with 25 g of 2-(2-hydroxyethoxy)phenol (0.16 mol.), 33 g of triethylamine (0.32 mol.), 250 ml of tetrahydrofuran and 1 g of phenothiazine. Next, 30 g of acryloyl chloride (0.18 mol.) was slowly added to the reaction over 1 hour via the addition funnel. The triethylamine hydrochloride salt was removed by filtration and the mother liquor was evaporated with a rotoevaporator. The remaining liquid was dissolved in chloroform and washed with NaCl(aq.), NH$_4$OH(10%), NaCl(aq.) and dried over MgSO$_4$. The chloroform was removed with a rotoevaporator to yield 26 g (62%) of a reddish brown liquid. The product was confirmed by IR and $^{13}$C NMR.

Example 3

N,N,-Di(acryloyloxyethyl)-N,N'-dimethyl phthalamide (DAMP)

A one liter, three necked flask was equipped with an overhead stirrer, nitrogen atmosphere and an addition funnel. The flask was charged with 148 g of 2-(methylamino) ethanol (1.97 mol.) and 600 ml of dichloromethane. The flask was cooled with an ice bath. Next, 100 g of phthaloyl chloride (0.49 mol.) was slowly added via the addition funnel over 5.5 hours. The dichloromethane was washed with NaCl(aq.). Next, the NaCl(aq.) layer was extracted with dichloromethane and the two dichloromethane layers were combined. The organic layer was evaporated with a rotoevaporator to yield 76 g (55%) of phthalamide diol.

A one liter, three necked flask was equipped with overhead stirrer, nitrogen atmosphere and an addition funnel. The flask was charged with 100 g of N,N'-di(hydroxyethyl)-N,N'-dimethyl phthalamide (0.36 mol.), 67.8 g of triethylamine (0.72 mol.), 500 ml of tetrahydrofuran and 2 g of phenothiazine. Next, 68 g of acryloyl chloride (0.75 mol.) was slowly added to the flask over one hour. The reaction was stirred for an additional hour. The triethylamine hydrochloride salt was removed by filtration and the remaining mother liquor was evaporated with a rotoevaporator to yield a light brown liquid. The liquid was dissolved in chloroform and washed with NaCl(aq.), NH$_4$OH(10%), NaCl(aq.) and dried over MgSO$_4$. The chloroform was removed with a rotoevaporator to yield 60 g (43%) of a light brown liquid. The product was confirmed by IR and $^{13}$C NMR.

Example 4

N-(Acryloyloxyethoxyethyl)hexahydrophthalimide (6HPIEEA)

A 500-ml, two necked flask was equipped with a magnetic stirring bar, heating mantle and condenser. The flask was charged with 51 g of 2-(aminoethoxy) ethanol (0.49 mol.) and 250 ml of ethanol. Next, 75 g of hexahydrophthalic anhydride (0.49 mol.) was slowly added to the flask. After the addition was complete the reaction was refluxed for 12 hours. The IR spectrum indicated the reaction was complete. The ethanol was removed with a rotoevaporator to yield 113 g (96%) of N-(2-hydroxyethoxyethyl) hexahydrophthalimide.

A one liter, three necked flask was equipped with overhead stirrer, nitrogen atmosphere and an addition funnel. The flask was charged with 100 g of N-(2-hydroxyethoxyethyl)hexahydrophthalimide (0.41 mol.), 42 g of triethylamine (0.41 mol.), 1 g of phenothiazine and 400 ml of acetone. Next, 38 g of acryloyl chloride (0.41 mol.) was added slowly to the flask via the addition funnel over 45 minutes. The reaction was stirred for an additional 12 hours. The triethylamine hydrochloride salt was removed by filtration and the remaining mother liquor was evaporated with a rotoevaporator. The resulting red-orange liquid was dissolved in chloroform and extracted with HCl(10%), NaCl (aq.), NH$_4$OH(10%), NaCl(aq.) and dried over MgSO$_4$. The chloroform was removed with a rotoevaporator to yield 72 g (59%) of an orange-red liquid. The product was confirmed by IR and $^{13}$C NMR.

Example 5

N-[2,3-Di(acryloyloxy)propyl] hexahydrophthalimide (6HPIDA)

A 500-ml, two necked flask was equipped a magnetic stirring bar, heating mantle and condenser. The flask was charged with 46 g of 3-amino-1,2-propanediol (0.50 mol.) and 300 ml of ethanol. Next, 77 g of hexahydrophthalic anhydride (0.50 mol.) was slowly added to the flask after which the reaction was refluxed for 12 hours. The imide formation was confirmed by IR. The ethanol was removed by a rotoevaporator to yield 92 g (81%) of the N-[2,3-di(hydroxy)propyl]hexahydrophthalimide.

A one liter, three necked flask was equipped with overhead stirrer, nitrogen atmosphere and an addition funnel. The flask was charged with 70 g of N-[2,3-di(hydroxy)propyl]hexahydrophthalimide (0.34 mol.), 69 g of triethylamine (0.34 mol.), 2 g of 4-dimethylaminopyridine, 500 ml of acetone and 0.5 g of phenothiazine. Next, 62 g of acryloyl chloride (0.68 mol.) was added over 1.5 hours via the addition funnel. The reaction was stirred an additional 12 hours at room temperature (about 20° C.). The triethylamine hydrochloride salt was removed by filtration and the mother liquor was evaporated with a rotoevaporator. The resulting liquid was dissolved in chloroform and washed with NaCl (aq.), NH$_4$OH(10%), NaCl(aq.) and dried over MgSO$_4$. The chloroform was removed with a rotoevaporator to yield 80 g (90%) of an orange-red liquid. The product was shown by IR and $^{13}$C NMR to be 85% N-[2,3-di(acryloyloxy)propyl] hexahydrophthalimide and 15% N-[(2-hydroxy-3-acryloyloxy)propyl]hexahydrophthalimide.

Example 6

2-[(N-Acryloyloxyethyl)-N-methyl]furanamide (FAEA)

A one liter, three necked flask was equipped with overhead stirrer, nitrogen atmosphere and an addition funnel. The flask was charged with 115 g of 2-(methylamino)ethanol (1.53 mol.) and 500 ml of dichloromethane. The reaction flask was cooled with an ice bath. Next, 100 g of furoyl chloride (0.77 mol.) was slowly added via the addition funnel over 2.5 hours. The dichloromethane was washed with NaCl(aq.). Next, the NaCl(aq.) layer was extracted with dichloromethane and the two dichloromethane layers were combined and dried over MgSO$_4$. The dichloromethane was removed with a rotoevaporator to yield 75 g (44%) of N-(2-hydroxyethyl)-N-methylfuranamide.

A one liter, three necked flask was equipped with overhead stirrer, nitrogen atmosphere and an addition funnel. The flask was charged with 75 g of N-(2-hydroxyethyl)-N-methylfuranamide (0.44 mol.), 50 g of triethylamine (0.44 mol.), 500 ml of tetrahydrofuran and 2 g of phenothiazine. Next, 40 g of acryloyl chloride (0.44 mol.) was slowly added to the reaction over 1.5 hours via the addition funnel. The reaction was stirred at room temperature (about 25° C.) for 1 hour. The triethylamine hydrochloride salt was removed by filtration and the mother liquor evaporated with a rotoevaporator. The remaining liquid was dissolved in chloroform and washed with NaCl(aq.), NH$_4$OH(10%), NaCl(aq.) and dried over MgSO$_4$. The chloroform was removed with a rotoevaporator to yield 86 g (87%) of a light brown liquid. The product was confirmed by IR and $^{13}$C NMR.

Example 7

2-(Acryloyloxyethyl)thenoate (ThEA)

A five liter, three necked flask was equipped with overhead stirrer, nitrogen atmosphere and an addition funnel. The flask was charged with 238 g of 2-hydroxyethylacrylate (2.04 mol.), 207 g of triethylamine (2.04 mol.), 1500 ml of tetrahydrofuran and 10 g of phenothiazine. Next, 300 g of 2-thiophenecarbonylchloride (2.04 mol.) was slowly added to the reaction over 3 hours via the addition funnel. The reaction was stirred 12 hours at room temperature (about 20° C.). The triethylamine hydrochloride salt was removed by filtration and the mother liquor evaporated with a rotoevaporator. The remaining liquid was distilled and 337 g (73%) was collected at 120°–123° C. @5 mmHg. The product was confirmed by IR and $^{13}$C NMR.

Example 8

5-(Acryloyloxyethyl)-4-methylthiazole (MTA)

A one liter, three necked flask was equipped with overhead stirrer, nitrogen atmosphere and an addition funnel. The flask was charged with 100 g of 5-(2-hydroxyethyl)-4-methylthiazole (0.70 mol.), 71 g of triethylamine (0.70 mol.), 500 g of chloroform and 3 g of phenothiazine. Next, 63 g of acryloyl chloride (0.70 mol.) was slowly added to the reaction over 1.5 hour via the addition funnel. The reaction was stirred for 2 hours at room temperature. The reaction mixture was extracted with NaCl(aq.), NH$_4$OH(10%), NaCl (aq.) and dried over MgSO$_4$. The chloroform was evaporated with a rotoevaporator to yield 113 g (82%) of a dark brown liquid. The product was confirmed by IR and $^{13}$C NMR.

Example 9

2-[N,N-Di(acryloyloxyethyl)]thiopheneamide (ThDEAA)

A one liter, three necked flask was equipped with overhead stirrer, nitrogen atmosphere and an addition funnel. The flask was charged with 143 g of diethanolamine (0.68 mol.) and 500 ml of dichloromethane. The reaction flask was cooled with an ice bath. Next, 100 g of 2-thiophenecarbonylchloride (0.68 mol.) was slowly added to the reaction over 4 hours via the addition funnel. The reaction was stirred for 12 hours at room temperature (about 20° C.). The dichloromethane reaction mixture was washed with NaCl(aq.). Next, the NaCl(aq.) layer was extracted with dichloromethane. The two dichloromethane layers were combined and dried over MgSO$_4$. The dichloromethane was removed with a rotoevaporator to yield 93 g (64%) of 2-[N,N'-di(2-hydroxyethyl)]thiopheneamide.

A one liter, three necked flask was equipped with overhead stirrer, nitrogen atmosphere and an addition funnel. The flask was charged with 85 g (64%) of 2-[N,N'-di(2-hydroxyethyl)]thiopheneamide (0.40 mol.), 80 g of triethylamine (0.80 mol.), 500 ml of tetrahydrofuran and 1 g of phenothiazine. Next, 72 g of acryloyl chloride (0.80 mol.) was slowly added to the reaction over 1.5 hours. The reaction was stirred at room temperature for 12 hours. The triethylamine hydrochloride salt was removed by filtration and the mother liquor evaporated with a rotoevaporator. The remaining liquid was dissolved in chloroform and washed with NaCl(aq.), NH$_4$OH (10%), NaCl(aq.) and MgSO$_4$. The chloroform was removed with a rotoevaporator to yield 58 g (45%) of a light red liquid. The product was confirmed by IR and $^{13}$C NMR.

Example 10

5-Acryloyloxymethyl-oxazolidin-2-one (OXA)

To a three liter flask equipped with a paddle stirrer, thermometer and addition funnel was added 91.5 g (1.0 mol.) of 3-amino-1,2-propanediol, followed by 2.2 moles of 12.5% aqueous NaOH. The solution was chilled with an ice bath to 0° C. as a solution of 100 g of phosgene in 400 ml of toluene was added over a 30 minute period. The solution was allowed to stir overnight, while coming to room temperature. The toluene layer was discarded and the aqueous layer was stripped on a rotoevaporator to a pasty liquid. Several hundred milliliters of ethanol were added. The paste was triturated and filtered. The ethanol solution was concentrated on a rotoevaporator to give 105 g (90%) of a nearly colorless oil, identified by $^{13}$C NMR to be 5-hydroxymethyl-oxazolidin-2-one.

105 g (0.90 mol.) of 5-hydroxymethyl-oxazolidin-2-one were placed into a one liter, three necked, round bottomed flask equipped with a paddle stirrer and thermometer. This was followed by 500 ml of tetrahydrofuran, 101 g (1.0 mol.) of triethylamine and 0.5 g of phenothiazine. Stirring was started as 90 g (1.0 mol.) of acryloyl chloride were added dropwise in such a way that the contents of the flask were maintained at 30° C. or less. When the addition was complete, the contents were stirred overnight at room temperature. The triethylamine hydrochloride was filtered and the solution was allowed to stand over NaHCO$_3$ and Na$_2$SO$_4$. The solution was filtered, transferred to a one liter, round bottomed flask and placed on a rotoevaporator. The solution was concentrated by purging with a stream of air while rotating the flask. The resulting liquid was confirmed by $^{13}$C NMR to contain a mixture of the desired product and unreacted starting material.

Examples 11–21

Use of Aromatic Acrylates as Reactive Diluents in Acrylamide Resins

In Examples 11–21, acrylamidomethyl novolak (AMN), produced in accordance with U.S. Pat. No. 5,236,472, acrylamidomethylated glycoluril (GUAM), produced in accordance with U.S. Pat. No. 5,055,113, and acrylamidomethylated phenol (AMP), produced in accordance with U.S. Pat. No. 4,903,440, were used in various resin formulations with the inventive reactive diluent compounds as detailed in Table 1. In each example, the resin/reactive diluent was coated onto a glass microscope slide as explained above in the "Knoop Hardness Test", and the hardness was tested after UV cure and after UV cure plus thermal post cure.

TABLE 1

| Example No. | Parts Resin | Parts Reactive Diluent | UV cure (KNH) | UV cure + heat (KHN) |
|---|---|---|---|---|
| 11 | 50 AMN | 50 CTA | 35 | 37 |
| 12 | 60 AMP | 40 DAMP | 33 | 35 |
| 13 | 60 AMP | 40 DAEP* | 34 | 34 |
| 14 | 60 AMP | 40 DAPP | 30 | 34 |
| 15 | 30 AMN, 30 GUAM | 40 DAP | 31 | 34 |
| 16 | 60 AMP | 40 SEA | 33 | 34 |
| 17 | 30 AMN, 30 GUAM | 40 PMMA | 26 | 33 |
| 18 | 60 AMP | 40 BA** | 26 | 25 |
| 19 | 60 AMP | 40 PEA** | 26 | 31 |
| 20 | 60 AMP | 40 BEA | 32 | 36 |
| 21 | 60 AMP | 40 PPEDA | 23 | 36 |

*"DAEP" is N,N'-di(acryloyloxyethyl)-N,N'-diethylphthalamide.
**Commercially available from Sartomer Company, Exton, PA, wherein "BA" is benzylacrylate, and "PEA" is phenoxyethyl acrylate Examples 22–28

Use of Imide Acrylates as Reactive Diluents in Acrylamide Resins

Examples 22–28 were performed essentially the same as Examples 11–21 with the exception that different reactive diluents were employed as detailed in Table 2.

TABLE 2

| Example | Parts Resin | Parts Reactive Diluent | UV cure (KHN) | UV cure + heat (KHN) |
|---|---|---|---|---|
| 22 | 60 AMP | 40 6HPIPA | 19 | 29 |
| 23 | 60 AMP | 40 4HPIDA | 30 | 35 |
| 24 | 60 AMP | 40 6HPIDA | 32 | 37 |
| 25 | 60 AMP | 40 MNIA | 35 | 38 |
| 26 | 60 AMP | 40 6HPIA | 36 | 38 |
| 27 | 60 AMP | 40 4HPIA | 37 | 38 |
| 28 | 60 AMP | 40 6HPIEEA | 17 | 31 |

Examples 29–50

Use of Heterocyclic Acrylates as Reactive Diluents in Acrylamide Resins

Examples 29–50 were essentially the same as Examples 11–28 except for the use of heterocyclic acrylate reactive diluents, as detailed in Table 3.

TABLE 3

| Example No. | Parts Resin | Parts Reactive Diluent | UV cure (KHN) | UV cure + heat (KHN) |
|---|---|---|---|---|
| 29 | 60 AMP | 40 ThEA | 32 | 42 |
| 30 | 60 AMP | 40 FEA | 14 | 31 |
| 31 | 60 AMP | 40 OXDA | 35 | 40 |
| 32 | 60 AMP | 40 OXA | 25 | 38 |
| 33 | 60 AMP | 40 ThMAA | 4 | 18 |
| 34 | 60 AMP | 40 ThEAA | 16 | 35 |
| 35 | 60 AMP | 40 ThPAA | 18 | 30 |
| 36 | 60 AMP | 40 ThDEAA | 35 | 42 |
| 37 | 60 AMP | 40 FDEAA | 26 | 34 |
| 38 | 30 AMN, 30 GUAM | 40 GCA | 32 | 37 |
| 39 | 30 AMN, 30 GUAM | 40 KDM | 27 | 29 |
| 40 | 30 AMN, 30 GUAM | 40 KEM | 23 | 26 |
| 41 | 30 AMN, 30 GUAM | 40 KCP | 25 | 29 |
| 42 | 30 AMN, 30 GUAM | 40 KDME | 24 | 28 |
| 43 | 30 AMN, 30 GUAM | 40 KEEM | 23 | 27 |
| 44 | 60 AMP | 40 OXE | 26 | 34 |
| 45 | 60 AMP | 40 PYA | 34 | 38 |
| 46 | 60 AMP | 40 AMORPH | 32 | 44 |
| 47 | 60 AMP | 40 AMA | 18 | 24 |
| 48 | 60 AMP | 40 PEAA | 4 | 4 |
| 49 | 30 AMN, 30 GUAM | 40 RDUA | 13 | 36 |
| 50 | 60 AMP | 40 FAEA | 5 | 31 |

Although the above examples are intended to be representative of the invention, they are not intended to limit the scope of the appended claims.

What is claimed is:

1. Organic compounds having at least one ethylenically-unsaturated group and being suitable for use as reactive diluents, said compounds being N-substituted succinimide derivatives of formula (III):

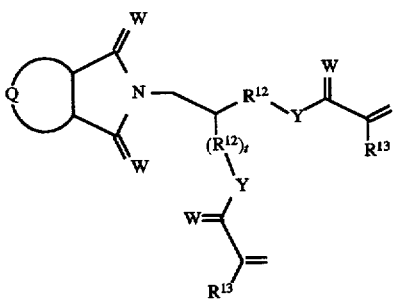

(III)

wherein:

R$^{12}$ is selected from the group consisting of —C$_x$H$_{2x}$— and —(C$_y$H$_{2y}$)—O—(C$_{y'}$H$_{2y'}$), wherein x is an integer ranging from 1 to 12 inclusive and y and y' are independently an integer ranging from 1 to 6 inclusive;

R$^{13}$ is H;

W is selected from the group consisting of O, S, NR$^{13}$; Y is selected from the group consisting of O, S, NR$^{14}$;

R$^{14}$ is selected from the group consisting of H, —C$_x$H$_{2x+1}$— wherein x is an integer ranging from 1 to 12 inclusive, —C(=O)—C(R$^{13}$)=CH$_2$, and —R$^{12}$—O—C(=O)—C(R$^{13}$)=CH$_2$;

Q is an organic radical which forms phthalimide, hexahydrophthalimide, tetrahydrophthalimide, or derivatives thereof with an N-substituted succinimide ring; and t is 0 or 1.

2. Compounds in accordance with claim 1 wherein a plurality of ethylenically unsaturated groups are present in the compound.

3. Compounds in accordance with claim 1 wherein the number of ethylenically unsaturated groups in the compound ranges from 1 to 10.

4. Compounds selected from the group consisting of cyclic imides within general formula (VI):

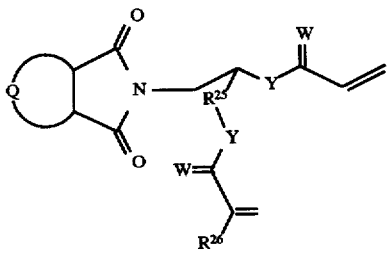

(VI)

wherein:

Q is an organic radical which forms phthalimide, hexahydrophthalimide, tetrahydropthalimide, or derivatives thereof with an N-substituted succinimide ring;

W is selected from the group consisting of NR$^{27}$, O, and S;

Y is selected from the group consisting of O, S, and NR$^{28}$;

R$^{25}$ is selected from the group consisting of —C$_x$H$_{2x}$— and —(C$_y$H$_{2y}$)—)—(C$_{y'}$H$_{2y'}$), wherein x is an integer ranging from 1 to 12 inclusive and y and y' are independently an integer ranging from 1 to 6 inclusive;

R$^{26}$ is —H;

R$^{27}$ is selected from the group consisting of H and —C$_x$H$_{2x+1}$;

R$^{28}$ is selected from the group consisting of H, —C$_x$H$_{2x+1}$, —C(=W)—C=CH$_2$, and C$_x$H$_{2x}$—O—C(=W)—C=CH$_2$; and wherein for R$^{27}$ and R$^{28}$, x ranges from 1 to 10 inclusive;

R$^{27}$ and R$^{28}$ may be the same or different.

5. Carbocyclic imides selected from the group consisting of compounds within general formula (XII):

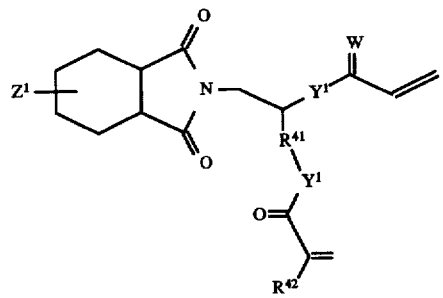

(XII)

wherein:

Z$^1$ is selected from the group consisting of H, and —C$_x$H$_{2x+1}$ wherein x ranges from 1 to 10 inclusive;

Y$^1$ is selected from the group consisting of NR$^{43}$ and O;

W is selected from the group consisting of O, S, NR$^{42}$;

R$^{41}$ is selected from the group consisting of —C$_x$H$_{2x}$— and —(C$_y$H$_{2y}$)—O—(C$_{y'}$H$_{2y'}$), wherein x is an integer ranging from 1 to 12 inclusive and y and y' are independently an integer ranging from 1 to 6 inclusive;

R$^{42}$ is —H;

R$^{43}$ is selected from the group consisting of —H, —C$_x$H$_{2x+1}$, —C(=W)—CH=CH$_2$, and —C$_x$H$_{2x}$—O—C(=W)—CH=CH$_2$ wherein x ranges from 1 to 10 inclusive.

6. Compounds selected from the group consisting of:

N-[2,3-Di(acryloyloxy)propyl]tetrahydrophthalimide;

N-[2,3-Di(acryloyloxy)propyl]hexahydrophthalimide; and

N-[2,3-Di(acryloyloxy)propyl]methyl nadimide.

7. A coatable, addition polymerizable binder precursor composition comprising:

(a) an addition polymerizable resin; and (b) an organic compound in accordance with claim 1.

8. A coatable, addition polymerizable binder precursor composition in accordance with claim 7 comprising a plurality of abrasive particles.

9. A coatable, addition polymerizable binder precursor composition comprising:

(a) an organic compound in accordance with claim 1; and (b) a plurality of abrasive particles.

* * * * *

UNITED STATES PATENT AND TRADEMARK OFFICE
CERTIFICATE OF CORRECTION

PATENT NO. : 5,710,281
DATED : January 20, 1998
INVENTOR(S) : Ernest L. Thurber, Eric G. Larson, Alan R. Kirk, and Gregg D. Dahlke It is certified that error appears in the above-identified patent and that said Letters Patent is hereby corrected as shown below:

Title page,
FOREIGN PATENT DOCUMENTS, "43-133491" should be -- 49-133491 --.

OTHER PUBLICATIONS, "pp. 287-321" should be -- pp. 306-321 --.

Column 3,
Line 38, "-0- (=0)" should be -- -0-C(=0) --.

Column 4,
Line 35, "$R^5$" should be -- $R^{15}$ --.

Column 13,
Line 22, after "-C(=O)-C=CH$_2$" should be -- -C(=O)-CH=CH$_2$ --.

Column 19,
Line 15, "$^3$C NMR" should be -- $^{13}$C NMR --.

Column 26, claim 4,
Line 6, "-C(=W)-C= CH$_2$" should be -- -C(=W)-CH= CH$_2$ --.
Line 6, "C$_x$H$_{2x}$-O-C(=W)-C=CH$_2$" should be -- C$_x$H$_{2x}$-O-C(=W)-CH=CH$_2$ --.

Signed and Sealed this

Twelfth Day of February, 2002

Attest:

JAMES E. ROGAN
Attesting Officer
Director of the United States Patent and Trademark Office